United States Patent [19]

Shapiro

[11] 4,178,917

[45] Dec. 18, 1979

[54] METHOD AND SYSTEM FOR NON-INVASIVE DETECTION OF ZINC PROTOPORPHYRIN IN ERYTHROCYTES

[76] Inventor: Howard M. Shapiro, 283 Highland Ave., West Newton, Mass. 02165

[21] Appl. No.: 866,788

[22] Filed: Jan. 3, 1979

[51] Int. Cl.² ............................................. A61B 5/00
[52] U.S. Cl. .................................... 128/665; 356/39; 356/317; 128/633
[58] Field of Search ............... 128/2 R, 2 A, 2 G, 2 L; 356/39–41, 317, 318

[56] References Cited

U.S. PATENT DOCUMENTS

| | | | |
|---|---|---|---|
| 3,136,310 | 6/1964 | Meltzer | 128/2 L |
| 3,463,142 | 8/1969 | Harte | 128/2 L |
| 3,638,640 | 2/1972 | Shaw | 128/2 L |
| 3,811,777 | 5/1974 | Chance | 128/2 L X |
| 3,825,342 | 7/1974 | Lubbers et al. | 356/41 |
| 4,029,085 | 6/1977 | DeWitt et al. | 128/2 R |

OTHER PUBLICATIONS

Blumberg et al, "The Hematofluorometer", Clinical Chemistry, vol. 23, No. 2, 1977.
Kobayashi et al, "Microfluorometry . . . In Situ," J. Applied Physiology, vol. 31, No. 5, Nov. 1971.
Shapiro et al, "Continuous Redox State . . . Organs," 26th, ACEMB, Minneapolis, Minn., Sep., 1973.

*Primary Examiner*—Lee S. Cohen
*Attorney, Agent, or Firm*—Kenway & Jenney

[57] ABSTRACT

A method and system for the non-invasive detection of zinc protoporphyrin (ZPP) in erythrocytes. Light at least partially within the fluorescence excitation spectrum of ZPP is directed onto the skin of a patient. The resultant incident light reflection and ZPP fluorescence from the region underlying the irradiated skin are detected. Signals representative of the detected light are generated and combined to provide a signal representative of the ZPP concentration in the erythrocytes within the sample region.

21 Claims, 2 Drawing Figures

METHOD AND SYSTEM FOR NON-INVASIVE DETECTION OF ZINC PROTOPORPHYRIN IN ERYTHROCYTES

BACKGROUND OF THE INVENTION

This invention relates to medical instrumentation, and more particularly, to a method and system for the noninvasive detection of zinc protoporphyrin in erythrocytes.

It has long been recognized that the ingestion of lead bearing compounds by humans may lead to lead poisoning. If such poisoning is not detected and treated, irreversible neurological damage may result. In the prior art, the measurement of lead in the blood has been the primary approach for detecting lead poisoning. However, this approach is difficult and relatively expensive to implement for large scale population screening. Recently, it has been recognized that the compound zinc protoporphyrin (ZPP) accumulates in erythrocytes (red blood cells) in humans exposed to low toxic levels of lead. It has further been observed that ZPP is characterized by a red fluorescence emission spectrum (having a strong peak at 590 nm and a weak peak at 640 nm) in response to excitation with blue light (at about 420 nm). In view of these observations, protoporphyrin fluorescence detection procedures have become accepted methods of screening for lead exposure. Furthermore, such procedures have also been determined to be effective in screening for iron deficiency anemia (such as may be due to bleeding, inadequate diet, heredity diseases) and for the detection of exposure to certain drugs, for example, the experimental anti-cancer agent cis-diamminedichloroplatinum.

In the prior art, ZPP fluorescence detection has been accomplished only using invasive techniques, that is, where a sample of blood is first obtained, and then analyzed using the ZPP fluorescence detection technique. This type of invasive procedure requires considerable effort in terms of obtaining samples, maintaining these samples, and performing and recording the test results. Accordingly, screening of medium to large size populations is quite difficult using the prior art approaches.

Accordingly, it is an object of the present invention to provide a method and system for performing the non-invasive detection of ZPP concentration in erythrocytes.

SUMMARY OF THE INVENTION

The present invention provides a method and system for the non-invasive detection of zinc protoporphyrin (ZPP) in erythrocytes (red blood cells) in a region underlying a sample surface of the patient. By way of example, the sample surface may be skin, conjunctiva, or mucous membranes. In accordance with the invention, a light source is directed to the skin of the patient. The spectrum of the source is at least partially within the fluorescence excitation spectrum of ZPP and outside the characteristic fluorescence emission spectrum of ZPP. The incident light passes through the skin and excites ZPP fluorescence in any red blood cells passing through blood vessels within the region underlying the sample surface. A portion of the red fluorescence emitted by ZPP passes from the region, through the skin and to a detector sensitive to light in the fluorescence emission spectrum of ZPP. The detector provides a signal related to the number of red blood cells passing through the region, as well as the level of ZPP in those cells. A second detector, which is sensitive to incident light within the spectrum of the source, is also coupled to the sample surface in order to measure light reflected (or scattered) from the red blood cells in the region. The second detector provides a signal related to the number of red blood cells passing through the region. The signals from the two detectors are combined to provide a signal representative of the concentration of ZPP in the erythrocytes.

BRIEF DESCRIPTION OF THE DRAWINGS

The foregoing and other objects of this invention, the various features thereof, as well as the invention itself, may be more fully understood from the following description, when read together with the accompanying drawings in which.

DESCRIPTION OF THE PREFERRED EMBODIMENT

Figure 1:
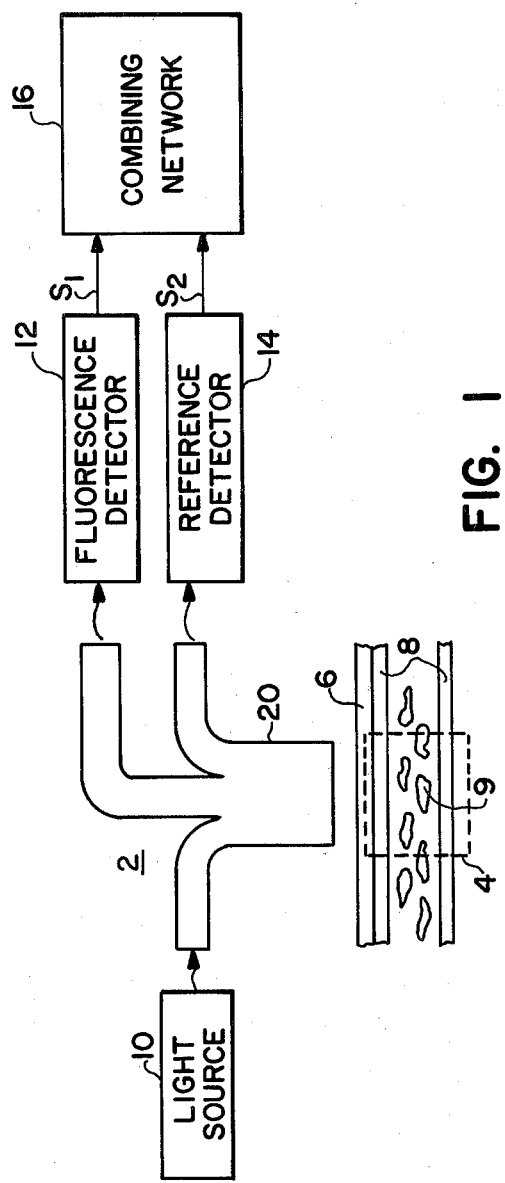
FIG. 1 shows in block diagram form an exemplary system according to the present invention.

FIG. 1 shows an exemplary embodiment of a system 2 for the non-invasive detection of ZPP in erythrocytes in a region 4 underlying a sample surface 6 of a patient in accordance with the present invention. The illustrated region 4 which underlies the sample surface 6 includes connective tissue and a blood vessel defined by walls 8. Red blood cells (represented by reference numeral 9) are transported by the plasma flowing within the blood vessel walls 8.

The system 2 includes a light source 10, including associated filters, for generating excitation light in the characteristic fluorescence excitation spectrum of ZPP. By way of example, a tungsten-halogen lamp emits sufficient light in the range 420–430 nm to serve as an adequate source for the fluorescence excitation. Alternatively, xenon or mercury or other arc lamps or blue light-emitting-diodes, or lasers operating in this spectral portion could be used in association with suitable filters. In response to light incident in its fluorescence excitation spectrum, ZPP emits light with a characteristic emission spectrum exhibiting a strong peak at 590 nm and a weak peak at 640 nm.

The system 2 further includes a fluorescence detector 12 for generating a signal $S_1$ representative of the intensity of light incident on that detector and in the characteristic fluoresence emission spectrum of ZPP. By way of example, the detector may take the form of a photomultiplier tube (having an S-1 or S-20 photocathode), or a solid state device, e.g. a phototransistor or photodiode operational amplifier combination. In conjunction with the detector, a broad-band color or interference filter may be used to limit the detector response to wavelengths in the range 590–680 nm. In alternative embodiments, the detector 12 may be adapted to respond to incident light within relatively narrow ranges including 590 nm or 640 nm, or both.

In addition, the system 2 includes a reference detector 14 for generating a signal $S_2$ representative of the intensity of light incident on that detector and the characteristic fluorescence excitation spectrum of ZPP.

In alternative embodiments, the source 10 may also generate light in some other band outside the ZPP emission spectrum, as well as within that spectrum, and the detector 14 may generate the signal $S_2$ representative of light incident thereon in that other band.

By way of example, source 10 may include a tungsten-halogen lamp and associated filter assembly adapted to emit light in the range 420–430 nm, and in addition include an infrared LED and associated filter assembly adapted to emit light at 900 nm, i.e. at a wavelength where the level which is back scattered from a skin sample, is relatively sensitive to changes in blood flow rate but insensitive to hemoglobin oxygenation. In this example, the fluorescence detector 12 generates signal $S_1$ in the same manner as described above, while the reference detector 14 is adapted to generate signal $S_2$ representative of 900 nm light incident thereon.

In the above embodiments, the signals $S_1$ and $S_2$ from detectors 12 and 14, respectively, are applied to a combining network 16 which generates a signal representative of a concentration of ZPP in the erythrocytes within the region 4. In the present embodiment, network 16 generates a signal proportional to the ratio $S_1/S_2$.

A light guide 20 is adapted to direct the excitation light from the source 10 to the sample skin surface 6 of a patient. Guide 20 is also adapted to transfer light emitted from the sample surface to be incident on the sensors of the fluorescence detector 12 and the reference detector 14. The light guide 20 may be conventionally constructed of a fiberoptics device in combination with suitable lenses and mirrors in order to minimize errors which might arise to variations in source-to-skin distance due to motion of the patient. However, in alternative embodiments, lens configurations alone may be suitable to guide the light between the source, detectors and sample skin surface.

In operation, the excitation light from source 10 is directed to pass through surface 6 into region 4. This light is attenuated, due to scattering and absorption, as it passes through the skin and tissue, by a factor which is substantially constant for relatively short observation periods. The excitation light is also scattered or reflected and to some extent absorbed by the red blood cells passing through that region. A portion of the scattered or reflected excitation light passes to the surface 6 where it is directed to the reference detector 14. The intensity of this light incident on the detector 14 varies with the number of red blood cells within region 4. As a result of these effects, the d.c. component of reference signal $S_2$ from detector 14 varies inversely with the amount of attenuation due to the tissue, while the a.c. component of that signal is proportional to the blood flow rate. Furthermore, the portion of the excitation light which is incident upon the red blood cells in region 4 excites the ZPP in those cells. A portion of the resultant fluorescence passes to the surface 6 where it is directed to fluorescence detector 12.

The fluorescence signal $S_1$ from detector 12 is proportional to the intensity of the fluorescence from the red blood cells passing through the region 4 during the observation interval. Since the transport of fluorescent substances into and out of region 4 is primarily due to the flow of red blood cells, the a.c. component of signal $S_1$ is proportional to the ZPP in the red blood cells passing through region 4. Since the background fluorescence and attenuation factors are relatively constant, the ratio signal provided by network 16 provides a measure of the ZPP concentration in the red blood cells passing through the region 4.

In an alternative form of the invention, the combining network 16 rectifies the signal $S_1$, eliminating the d.c. component due to interfering fluorescence, and scales that rectified signal by a factor inversely proportional to the amplitude of the d.c. component of $S_2$, thereby compensating for tissue attenuation.

Figure 2:
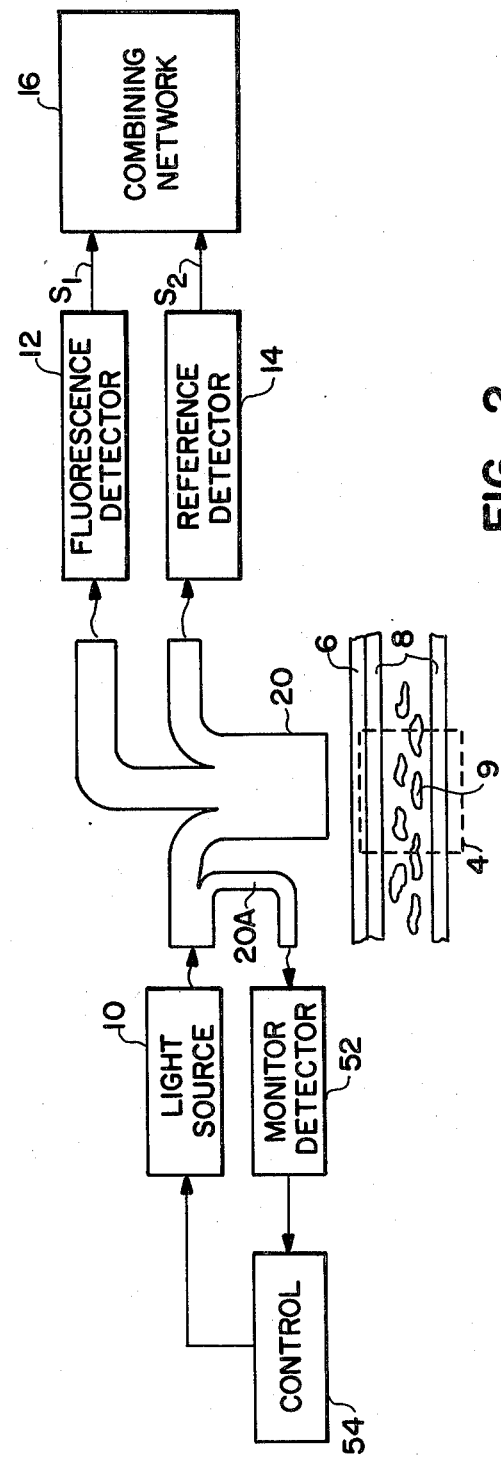
FIG. 2 shows in block diagram form an alternative embodiment of the present invention.

In practice, the intensity of illumination from source 10 may fluctuate with time. This effect may be minimized with use of a well-regulated power supply. Alternatively, the configuration shown in FIG. 2 may be utilized. This configuration is substantially the same as that shown in FIG. 1, but includes a control branch for the source 10. In FIG. 2, the light transfer device 20 includes a branch 20A for applying a portion of the light generated by source 10 to a monitor detector 52. Detector 52 produces an output signal proportional to the intensity of the light received by way of branch 20A. A control network 54 is responsive to the signal from the detector 52 to apply a control signal to source 10 to modify the output of that light source in a manner minimizing intensity fluctuations.

In these or other embodiments, compensation for blood flow fluctuations may be achieved by use of additional sources and scatter, reflectance or absorbance detectors operating at wavelength bands outside those of interest. Noise reduction may be achieved through the use of chopping or other source modulating techniques in conjunction with synchronous detection techniques.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

I claim:

1. A system for the non-invasive detection of zinc protoporphyrin (ZPP) in erythrocytes in a region underlying a sample surface of a patient, comprising:
    A. source means for generating excitation light in a predetermined spectrum, said predetermined spectrum being outside the characteristic fluorescence emission spectrum of ZPP and at least a portion of said predetermined spectrum being in the characteristic fluorescence excitation spectrum of ZPP,
    B. first detection means for generating a first signal representative of the intensity of light incident thereon and in said characteristic fluorescence emission spectrum of ZPP,
    C. second detection means for generating a second signal representative of the intensity of light incident thereon and within said predetermined spectrum,
    D. transfer means for directing said excitation light to be incident on said sample surface, and for directing light emitted from said sample surface to be incident on said first and second detection means,
    E. circuit means responsive to said first and second signals to generate a signal representative of the concentration of ZPP in said erythrocytes.

2. The system according to claim 1 further comprising:
    third detection means for generating an excitation level signal representative of the intensity of light incident thereon and in said fluorescence excitation spectrum, monitor transfer means for directing a predetermined portion of said excitation light to be incident on said third detection means, wherein said excitation level signal is representative of the intensity of said excitation light.

3. The system according to claim 2 further comprising:

source control means responsive to said excitation level signal to adaptively control said source means whereby the intensity of said light incident in said third detection means is substantially constant.

4. The system according to claim 1 wherein said circuit means comprises:

means responsive to said first signal to generate a third signal representative of the amplitude of the a.c. component of said first signal, means responsive to said second signal to generate a fourth signal representative of the amplitude of the a.c. component of said second signal, means responsive to said third and fourth signals to generate a fifth signal representative of the ratio of said third and fourth signals, said fifth signal being representative of the concentration of ZPP in said erythrocytes.

5. The system according to claim 1 wherein said circuit means comprises means responsive to said first and second signals to generate a ZPP signal representative of the ratio of said first and second signals, said ZPP signal being representative of the concentration of ZPP in said erythrocytes.

6. The system according to claim 1 wherein said source means is adapted to generate said excitation light at wavelengths substantially in the range 420–430 nm.

7. The system according to claim 6 wherein said first detection means is adapted to be responsive to incident light having wavelengths substantially in the range 590–680 nm.

8. The system according to claim 7 wherein said second detection means is adapted to be responsive to incident light having wavelengths substantially in the range 420–430 nm.

9. The system according to claim 6 wherein said first detection means is adapted to be responsive to incident light having wavelengths substantially in a relatively narrow range including 590 nm.

10. The system according to claim 9 wherein said second detection means is adapted to be responsive to incident light having wavelengths substantially in the range 420–430 nm.

11. The system according to claim 6 wherein said first detection means is adapted to be responsive to incident light having wavelengths substantially in a relatively narrow range including 640 nm.

12. The system according to claim 11 wherein said second detection means is adapted to be responsive to incident light having wavelengths substantially in the range 420–430 nm.

13. The system according to claim 1 wherein said predetermined spectrum is substantially all within said characteristic excitation spectrum.

14. The system according to claim 1 wherein said predetermined spectrum includes at least a portion outside said characteristic excitation spectrum and wherein said second detection means is adapted whereby said second signal is representative of the intensity of light incident thereon and in said portion outside said characteristic excitation spectrum.

15. Method for the non-invasive detection of zinc protoporphyrin (ZPP) in erythrocytes in a region underlying a sample surface of a patient, comprising the steps of:

A. generating excitation light in a predetermined spectrum, said predetermined spectrum being outside the characteristic fluorescence emission spectrum of ZPP and at least partially in the characteristic fluorescence excitation spectrum of ZPP, B. directing said excitation light to be incident on said sample surface, C. detecting light emitted from said sample surface in said characteristic fluorescence emission spectrum of ZPP and generating a first signal representative of the intensity thereof, D. detecting light emitted from said sample surface in said predetermined spectrum and generating a second signal representative of the intensity thereof, E. combining said first and second signals generating a signal representative of the concentration of ZPP in said erythrocytes.

16. The method according to claim 15 comprising the further step of:

generating an excitation level signal representative of the intensity of a predetermined portion of said excitation light.

17. The method according to claim 16 comprising the further step of:

adaptively controlling said step of generating of excitation light in response to said excitation level signal whereby the intensity of said light incident on said sample surface is substantially constant.

18. The method according to claim 15 wherein said combining step comprises:

generating a third signal from said first signal, said third signal being representative of the amplitude of the a.c. component of said first signal, generating a fourth signal from said second signal, said fourth signal being representative of the amplitude of the a.c. component of said second signal, combining said third and fourth signals to generate a fifth signal representative of the ratio of said third and fourth signals, said fifth signal being representative of the concentration of ZPP in said erythrocytes.

19. The method according to claim 15 wherein said combining step comprises combining said first and second signals to generate a ZPP signal representative of the ratio of said first and second signals, said ZPP signal being representative of the concentration of ZPP in said erythrocytes.

20. The method according to claim 15 wherein said predetermined spectrum is substantially within said characteristic fluorescence excitation spectrum of ZPP.

21. The method according to claim 15 wherein said predetermined spectrum is at least partially outside said characteristic excitation spectrum, and wherein said step D comprises the step of:

detecting light in the portion of said predetermined spectrum outside said characteristic excitation spectrum and generating said second signal representative of the intensity thereof.

* * * * *